(12) United States Patent
Gerrard et al.

(10) Patent No.: US 8,736,267 B2
(45) Date of Patent: May 27, 2014

(54) PRESSURE VESSEL FOR NON-DESTRUCTIVE OR NON-CONTACT MATERIAL CHARACTERIZATION

(75) Inventors: David Peter Gerrard, Magnolia, TX (US); Omar H. Balcazar, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 368 days.

(21) Appl. No.: 13/169,434

(22) Filed: Jun. 27, 2011

(65) Prior Publication Data

US 2012/0326718 A1 Dec. 27, 2012

(51) Int. Cl.
*G01V 3/00* (2006.01)
(52) U.S. Cl.
USPC .......................................... 324/321; 324/315
(58) Field of Classification Search
USPC .................... 324/321, 322, 318, 315
See application file for complete search history.

(56) References Cited

U.S. PATENT DOCUMENTS

| 5,977,772 | A  | * | 11/1999 | Wand et al. ................ 324/321 |
| 6,749,749 | B2 | * | 6/2004  | Xie et al. ................... 210/198.2 |
| 7,049,817 | B2 | * | 5/2006  | Fleury et al. ............... 324/315 |

* cited by examiner

*Primary Examiner* — Louis Arana
(74) *Attorney, Agent, or Firm* — Cantor Colburn LLP

(57) ABSTRACT

A method and apparatus for measuring a parameter of an object is disclosed. The object is placed within a vessel configured to contain the object via an opening in the vessel. A cover is placed over the opening. A securing device is used to secure the cover to the vessel. A measurement device is used to measure the parameter of the object at a raised pressure. The parameter can be a nuclear magnetic resonance parameter of the object. A fluid in the vessel can be heated to raise the pressure within the sealed vessel. In various embodiments, the securing device can be a second cover or a clamp, for example. The measured parameter can be used in determining a suitability of the object for use in downhole environments.

20 Claims, 2 Drawing Sheets

PRESSURE VESSEL FOR NON-DESTRUCTIVE OR NON-CONTACT MATERIAL CHARACTERIZATION

BACKGROUND

Devices that are used in downhole environments tend to experience corrosion or wear due to the various conditions of the downhole environment, such as elevated temperatures, elevated pressures and the various chemicals found therein. Knowing how well a material can withstand the effects of the downhole environment can be informative when designing tools and components for downhole applications. Therefore, experiments are generally designed in which test objects are immersed in fluids obtained from downhole and pressures and temperatures are raised to reasonably simulate a downhole environment. Unfortunately, vessels for containing the test object need to be sealed to sufficiently maintain downhole conditions in the pressure vessel during the measurement process. The present disclosure provides a method and apparatus for sealing a pressure vessel to maintain downhole pressures within the pressure vessel.

BRIEF DESCRIPTION

In one aspect, the present disclosure provides a method of measuring a parameter of an object, including: covering an opening of a vessel containing the object using a first cover; securing the first cover to the vessel; raising a pressure within the sealed vessel; and measuring the parameter of the object at the raised pressure.

In another aspect, the present disclosure provides an apparatus for measuring a parameter of an object, including: a vessel configured to contain the object, the vessel having an opening; a first cover configured to cover the opening; a securing device configured to secure the first cover to the vessel; and a measurement device configured to measure the parameter of the object at a raised pressure.

In yet another aspect, the present discloses a method of sealing a vessel that includes plugging an opening of the vessel with a plug; covering the plugged opening of the vessel using a first cap; and covering a portion of the first cap with a second cap to seal the vessel.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
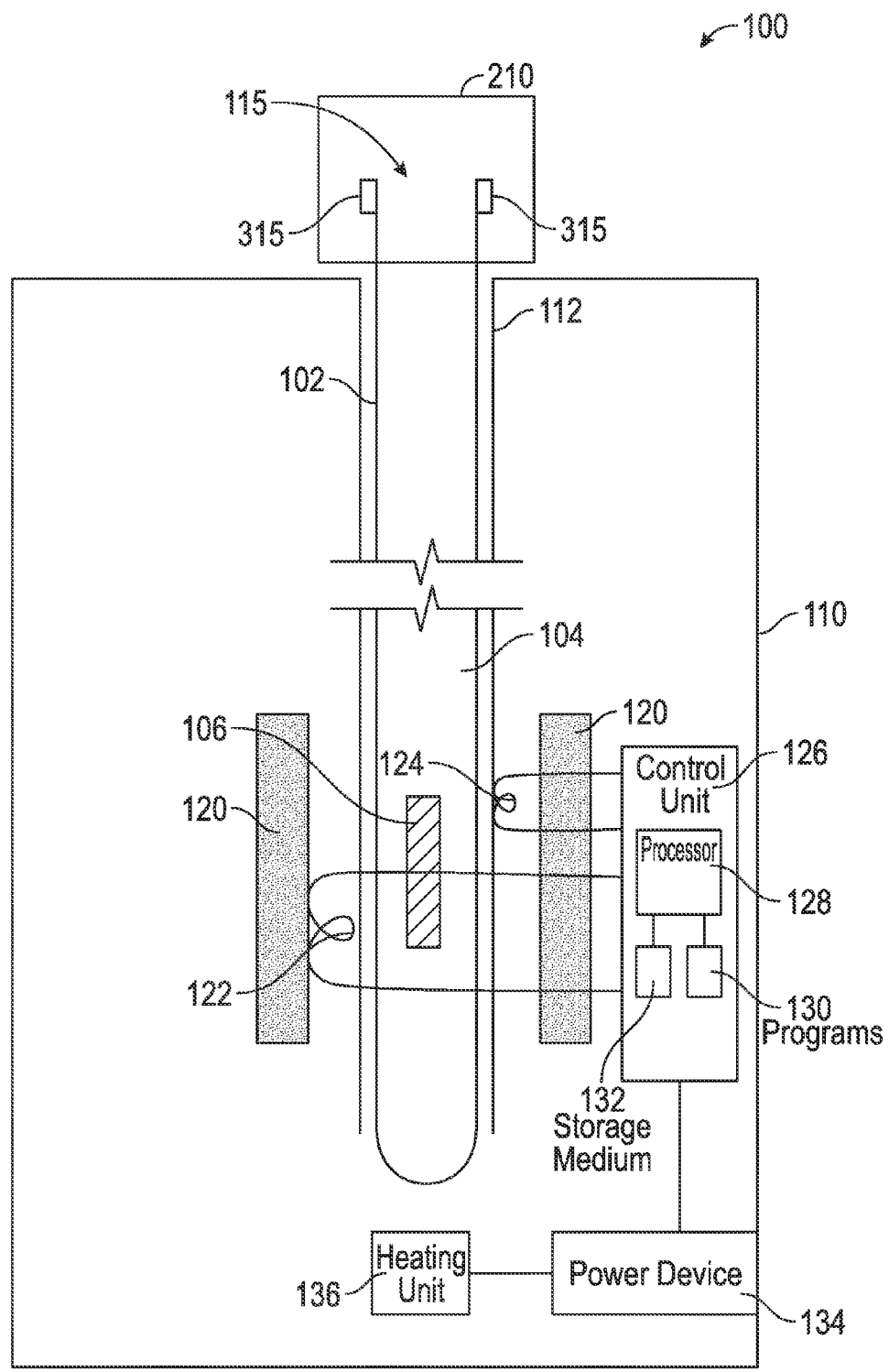
FIG. 1 shows an exemplary apparatus used to measure a parameter of an object contained in an exemplary pressure vessel of the present disclosure.

FIG. 1 shows an exemplary apparatus 100 used to measure a parameter of an object contained in an exemplary pressure vessel of the present disclosure. The apparatus 100 includes a measurement device 110 and a vessel 102 containing the test object. In one embodiment, the exemplary measurement device 110 can be a device for measuring a nuclear magnetic resonance parameter. However, the type of measurement device is not meant as a limitation of the present disclosure. The measurement device can be any device for characterization of material properties using non-destructive or non-contact methods, such as electromagnetic testing, acoustic testing, etc. The vessel 102 can hold a fluid 104 and the test object 106 for measurement purposes. The fluid is typically a fluid obtained from a downhole location such as formation fluids, wellbore fluids, etc. The test object is typically a component or portion of a component intended for use in a downhole environment. Measurements obtained from the test object can be used to determine the suitability for use downhole of a component made from the material of the test object.

In various aspects, the pressure vessel 102 is sealed with a cover assembly 210 with the fluid 104 and test object 106 therein. Temperature and pressure of the pressure vessel is raised to simulate a temperature and pressure typical of a downhole environment. Once the pressure vessel is sealed, the temperature inside the pressure vessel can be raised to thereby increase a vapor pressure within the pressure vessel. The exemplary pressure vessel 102 may be heated at a location separate from the apparatus 100 and/or may be heated while seated at the apparatus 100 using for example heating unit 136.

The pressure vessel may be placed into and removed from a receiving slot 112 of the measurement device 110 configured to hold the pressure vessel. In one embodiment, the measurement device is a nuclear magnetic resonance (NMR) device configured to determine various NMR parameters, such as a spin-lattice relaxation rate of the nuclei and a spin-spin relaxation rate of the nuclei, for example. In the exemplary NMR device, the magnet 120 is located alongside the receiving slot 112 and is configured to provide a static magnetic field within the pressure vessel in the receiving slot. The magnet can be a permanent magnet, an electro-magnet or a combination thereof. When the vessel is placed in the receiving slot, nuclei of the test object in the pressure vessel align in the direction of the static magnetic field after a certain relaxation time. A transmitter 122 is configured to transmit electromagnetic energy into the vessel at a frequency selected to excite the aligned nuclei of the specimen from their orientation along the direction of the static magnetic field. The transmitted electromagnetic energy is generally a radio frequency pulse known as an excitation pulse. A receiver 124 is configured to receive electromagnetic energy from the test object responsive to the transmitted electromagnetic energy from the transmitter. Controller 126 controls operation of the transmitter and receiver, for example by providing a selected excitation pulse to the transmitter. In an exemplary embodiment, the transmitter is an induction coil and the receiver is another induction coil. The transmitter and receiver coils are separately operated by various electronics, such as by the control unit 126. In another embodiment, the transmitter and the receiver can be the same induction coil, and the control unit 126 is configured to operate the coil in a transmitter mode and a receiver mode. The controller also includes a processor 128, various programs 130 stored on a computer-readable medium accessible to the processor and at least one storage medium 132 for storing a measured parameter of the test object, among other things. Typically the nuclear magnetic resonance parameter can be used to determine a property of the test object, such as its resiliency against wear in a downhole environment. Thus, the parameter can be used to characterize the specimen and determine the suitability of the specimen for use downhole. Power device 134 generally provides power to controller 126 and heating unit 136 as well as other components of the measurement device 110.

The exemplary pressure vessel 102 of FIG. 1 typically includes a tubular body with a closed end at one axial end of the pressure vessel and an opening axially opposite the closed end of the pressure vessel. The opening allows for specimen installation and removal. The closed end can be a rounded end. A protrusion 315 is generally located on an outer surface of pressure vessel at the opening 115. In various embodiments, the protrusion 315 can be a ring, lip, flange, band, etc. The pressure vessel is generally made of a material that is suitable for use in the measurement device 110, such as a borosilicate glass such as PYREX. Alternate embodiments of the pressure vessel are made of unreinforced or reinforced engineered thermoplastic such as TEFLON and/or PEEK, among others, depending on the operating internal pressures and temperatures and the type of sensing probe employed. In various embodiments, the pressure vessel is transparent to the electromagnetic energy of the excitation pulse transmitted by transmitter 122 to excite nuclei of the object. In an exemplary embodiment, the pressure vessel is 8.00 inches in length, has an inner diameter of about 8 mm and a wall thickness of about 1 mm Protrusion 315 typically has an outer diameter of about 13 mm and about 1 mm in axial length. Cover assembly 210 is shown coupled to the pressure vessel 102 at the opening 115 to the pressure vessel. Details of the cover assembly are discussed with respect to FIG. 2.

Figure 2:
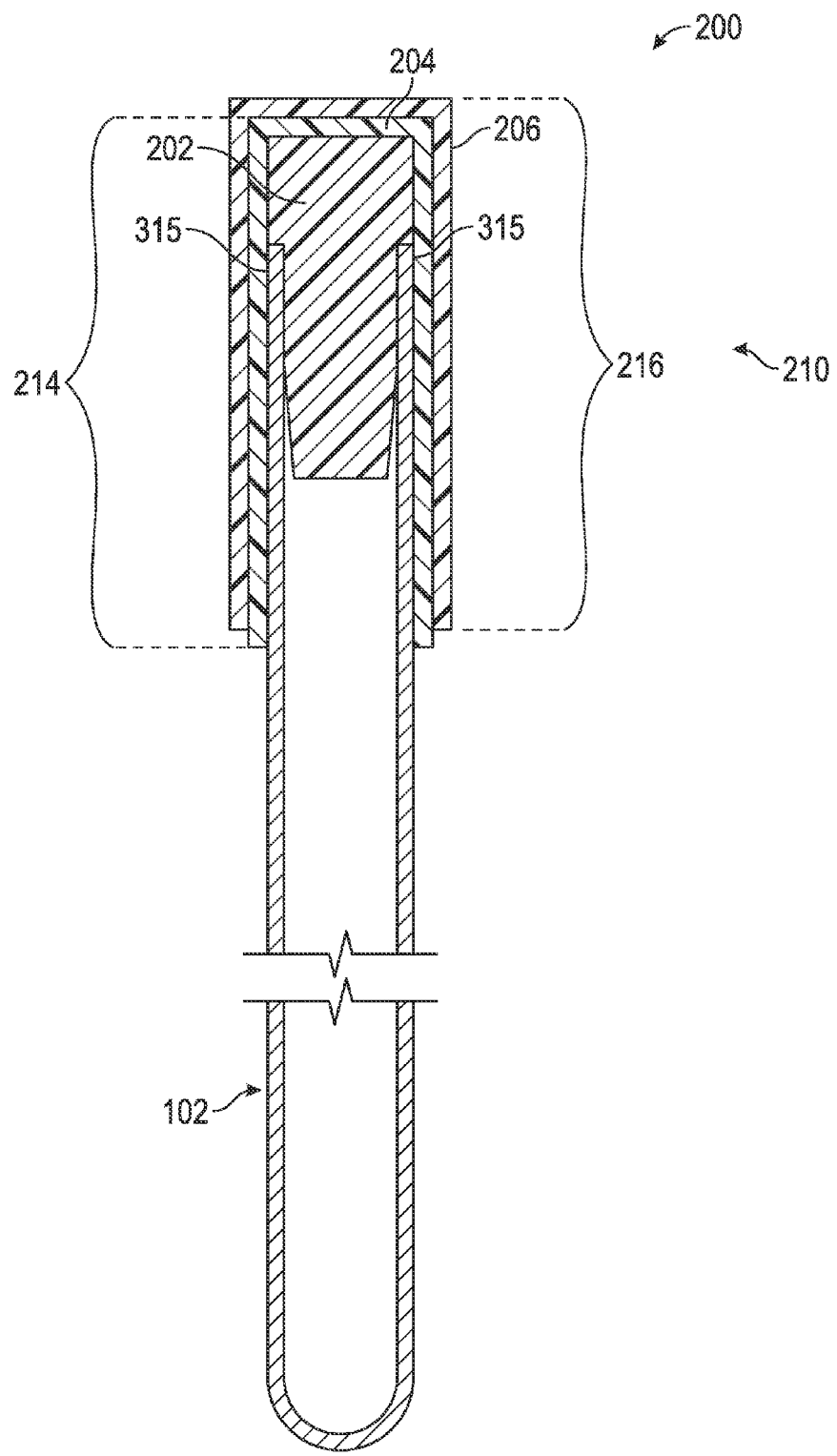
FIG. 2 shows a side view of the exemplary pressure vessel of FIG. 1 in an exemplary embodiment of the present disclosure.

FIG. 2 shows a side view of the exemplary pressure vessel assembly 200 of FIG. 1. The exemplary assembly 200 includes the exemplary vessel 102 and an exemplary cover assembly 210. Cover assembly 210 is configured to maintain a seal on the pressure vessel 102 at a raised pressure such as a pressure typical of a downhole environment or a pressure greater than about 400 psi. The cover assembly 210 can include a plug 202, a first cover (first cap) 204 and a second cover (second cap) 206. In an exemplary embodiment, one or more of the plug 202, first cap 204 and second cap 206 are made of ethylene propylene diene monomer (EPDM). Plug 202 is inserted into the opening 115 of the pressure vessel to plug the opening 115. In a particular embodiment, plug 202 has a conical section having a large diameter end and a small diameter end, wherein a diameter of the large diameter end is greater than an inner diameter of the opening and the diameter of the small diameter end is less than the inner diameter of the opening. In an exemplary embodiment, the large diameter end has a diameter of about 0.343 inches and the small diameter end has a diameter of about 0.250 inches. Exemplary plug 202 has a length of about 1 inch.

First cap 204 is placed over the opening 115 having the plug 202 therein and over a portion of an external surface of the pressure vessel. First cap 204 typically includes a sleeve portion 214 having a closed end at one axial end of the sleeve portion and an opening at an axial end opposed to the closed end. Typically an inner diameter of the sleeve portion 214 is substantially the same as an outer diameter of the pressure vessel 102 and therefore sleeve portion 214 generally conforms to the pressure vessel when the first cap is placed over the plugged opening of the pressure vessel. In an exemplary embodiment, the sleeve portion 214 is a cylindrical shell and conforms to a tubular body of the pressure vessel. The first cap 204 is configured to fit over the plug when the plug is forming a seal at the opening 315. The sleeve portion of the first cap is configured to extend axially over a length of the exterior surface of the pressure vessel when the first cap is fit over plug 202. The sleeve portion of the first cap couples to the exterior surface of the pressure vessel to provide a sealing force of the first cap at the pressure vessel. In various embodiments, the sleeve portion 214 extends axially along the outer face of the pressure vessel to cover the protrusion 115 at the opening of the pressure vessel. The sleeve portion 214 covering the protrusion 115 provides a sealing force between the sleeve portion and the protrusion. Exemplary first cap 204 has an inside diameter of 0.415 inches and a sleeve portion 214 that is about 1.5 inches in length.

Second cap 206 is placed over the first cap 204. Second cap 206 typically has a sleeve portion 216 that including a closed end and an open end axially opposed to the closed end. The inner diameter of the sleeve portion 216 of the second cap is substantially the same as the cross-section of the sleeve portion 214 of the first cap. Therefore, the second cap 206 is configured to fit over the first cap 204 and to secure the first cap 204 to the vessel. Thus, in alternate embodiments, any device configured to secure the first cap to the vessel can be used in place of the second cap. Such securing devices can include various clamps, such as a hose clamp. Returning to the second cap, the sleeve portion 216 of the second cap is configured to extend over the sleeve portion 214 of the first cap to provide a radially-inward force along the sleeve portion 214 of the first cap, thereby provides an additional sealing force between the sleeve portion 214 of the first cap and the outer surface of the pressure vessel. In various embodiments, the sleeve portion 216 of the second cap is configured to fit over the sleeve portion 214 of the first cap at the axial location of the protrusion of the pressure vessel to thereby provide an additional sealing force between the sleeve portion 214 of the first cap and the protrusion. Exemplary second cap 206 has an inside diameter of 0.535 inches and a sleeve portion 216 that is about 1.5 inches in length.

The exemplary pressure vessel 102 has been tested at 218° C. (425° F.), for 2 continuous hours, wherein the vessel was filled with water and roughly 430 psi of vapor pressure was generated. Caps, plugs and tube have been shown to be able to maintain 430 psi of pressure for 2 hours without defects.

Therefore, in one aspect, the present disclosure provides a method of measuring a parameter of an object, including: covering an opening of a vessel containing the object using a first cover; securing the first cover to the vessel; raising a pressure within the sealed vessel; and measuring the parameter of the object at the raised pressure. Raising the pressure within the sealed vessel typically includes heating a fluid contained in the sealed vessel. The method can include plugging the opening of the vessel with a plug and covering the opening and the plug with the first cover. In one embodiment, in an exterior face of the vessel includes a protrusion, and the method further includes covering the protrusion with the first cover. The first cover can be secured to the vessel using at least one of (i) a second cover; and (ii) a clamp. In one embodiment, the parameter is a nuclear magnetic resonance parameter of the object. Generally, the vessel is transparent to electromagnetic radiation at an excitation frequency of nuclei of the object. The pressure within the sealed vessel can be raised to greater than about 400 psi. A suitability of the object for use in a downhole environment can be determined using the measured parameter.

In another aspect, the present disclosure provides an apparatus for measuring a parameter of an object, including: a vessel configured to contain the object, the vessel having an opening; a first cover configured to cover the opening; a securing device configured to secure the first cover to the vessel; and a measurement device configured to measure the parameter of the object at a raised pressure. In an embodiment in which the vessel includes a fluid contained in the sealed vessel, a heat source can be used to heat the fluid in the sealed vessel to raise the pressure within the vessel. The apparatus can include a plug to plug the opening, wherein the first cover is configured to cover the opening and the plug in the opening. In one embodiment, the vessel includes a protrusion at an exterior face of the vessel and the first cover is configured to cover the protrusion. The securing device can be at least one of: (i) a second cover; and (ii) a clamp. In one embodiment, the parameter is a nuclear magnetic resonance parameter of the object. The vessel can therefore be transparent to electromagnetic radiation at an excitation frequency of nuclei of the object. The pressure in the sealed vessel can be raise to greater than about 400 psi. The apparatus can also include a processor configured to determine a suitability of the object for use in a downhole environment using the measured parameter.

In yet another aspect, the present discloses a method of sealing a vessel that includes plugging an opening of the vessel with a plug; covering the plugged opening of the vessel using a first cap; and covering a portion of the first cap with a second cap to seal the vessel. In an embodiment in which the vessel includes a protrusion on an outer surface of the vessel, the method further includes covering the protrusion with the first cap to provide a sealing force of the first cap to the vessel.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed:

1. A method of measuring a parameter of an object, comprising:
    covering an opening of a vessel containing the object using a first cover having a sleeve portion extending along a portion of an exterior surface of the vessel;
    securing the first cover to the vessel via a radially-inward force along the sleeve portion of the first cover;
    raising a pressure within the sealed vessel; and
    measuring the parameter of the object at the raised pressure.

2. The method of claim 1, wherein raising the pressure within the sealed vessel further comprises heating a fluid contained in the sealed vessel.

3. The method of claim 1, further comprising plugging the opening of the vessel with a plug and covering the opening and the plug with the first cover.

4. The method of claim 1, wherein an exterior face of the vessel includes a protrusion, further comprising covering the protrusion with the first cover.

5. The method of claim 1, further comprising securing the first cover to the vessel using at least one of (i) a second cover that fits over the first cover to provide a sealing force to the sleeve of the first cover; and (ii) a clamp.

6. The method of claim 1, wherein the parameter is a nuclear magnetic resonance parameter of the object.

7. The method of claim 6, wherein the vessel is transparent to electromagnetic radiation at an excitation frequency of nuclei of the object.

8. The method of claim 1, further comprising raising the pressure within the sealed vessel to greater than about 400 psi.

9. The method of claim 1, further comprising determining a suitability of the object for use in a downhole environment using the measured parameter.

10. An apparatus for measuring a parameter of an object, comprising:
    a vessel configured to contain the object, the vessel having an opening;
    a first cover configured to cover the opening, the first cover having a sleeve portion extending along a portion of an exterior surface of the vessel;
    a securing device configured to provide a radially-inward force along the sleeve of the first cover to secure the first cover to the vessel; and
    a measurement device configured to measure the parameter of the object at a raised pressure.

11. The apparatus of claim 10, wherein the vessel further includes a fluid in the sealed vessel, further comprising a heat source configured to heat the fluid in the sealed vessel to raise the pressure within the sealed vessel.

12. The apparatus of claim 10, further comprising a plug configured to plug the opening, wherein the first cover is configured to cover the opening and the plug in the opening.

13. The apparatus of claim 10, wherein the vessel includes a protrusion at an exterior face of the vessel and the first cover is configured to cover the protrusion.

14. The apparatus of claim 10, wherein the securing device further comprising at least one of: (i) a second cover that fits over the first cover to provide a sealing force to the sleeve of the first cover; and (ii) a clamp.

15. The apparatus of claim 10, wherein the parameter is a nuclear magnetic resonance parameter of the object.

16. The apparatus of claim 15, wherein the vessel is transparent to electromagnetic radiation at an excitation frequency of nuclei of the object.

17. The apparatus of claim 10, wherein the raised pressure is a pressure greater than about 400 psi.

18. The apparatus of claim 10, further comprising a processor configured to determine a suitability of the object for use in a downhole environment using the measured parameter.

19. A method of sealing a vessel, comprising;
    plugging an opening of the vessel with a plug;
    covering the plugged opening of the vessel using a first cap having a sleeve portion extending along a portion of an exterior surface of the vessel; and
    covering a portion of the first cap with a second cap to provide a radially-inward force along the sleeve portion of the first cover to seal the vessel.

20. The method of claim 19, wherein the vessel includes a protrusion on an outer surface of the vessel, further comprising covering the protrusion with the first cap to provide a sealing force of the first cap to the vessel.

* * * * *